(12) United States Patent
Russell et al.

(10) Patent No.: US 9,375,180 B2
(45) Date of Patent: Jun. 28, 2016

(54) UNIVERSAL PRESSURE TRANSDUCER MOUNTING DEVICE

(71) Applicants: John Russell, Cologne, MN (US); William J. Taylor, Woodbury, MN (US)

(72) Inventors: John Russell, Cologne, MN (US); William J. Taylor, Woodbury, MN (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 103 days.

(21) Appl. No.: 13/800,204

(22) Filed: Mar. 13, 2013

(65) Prior Publication Data

US 2013/0283921 A1    Oct. 31, 2013

Related U.S. Application Data

(60) Provisional application No. 61/639,940, filed on Apr. 29, 2012.

(51) Int. Cl.

| | |
|---|---|
| *G01L 7/00* | (2006.01) |
| *A61B 5/00* | (2006.01) |
| *G01L 7/18* | (2006.01) |
| *A61B 5/0215* | (2006.01) |
| *A61M 5/00* | (2006.01) |
| *G01L 19/14* | (2006.01) |
| *A61B 5/03* | (2006.01) |

(52) U.S. Cl.
CPC .............. *A61B 5/6887* (2013.01); *A61B 5/0215* (2013.01); *A61M 5/007* (2013.01); *G01L 7/00* (2013.01); *G01L 7/182* (2013.01); *G01L 19/14* (2013.01); *A61B 5/036* (2013.01); *A61B 2505/05* (2013.01)

(58) Field of Classification Search
None
See application file for complete search history.

(56) References Cited

U.S. PATENT DOCUMENTS

| 1,033,531 A | 7/1912 | Brown |
| 2,543,017 A | 2/1951 | Hagan |

(Continued)

FOREIGN PATENT DOCUMENTS

| CN | 88211436 U | 12/1988 |
| CN | 2341709 Y | 10/1999 |

(Continued)

OTHER PUBLICATIONS

Corrected International Preliminary Report on Patentability issued May 20, 2014 for PCT application No. PCT/US2013/038649, 18 pages.

(Continued)

*Primary Examiner* — Andre Allen
(74) *Attorney, Agent, or Firm* — Fredrikson & Byron, P.A.

(57) ABSTRACT

A pressure transducer mounting device may include a support member and a pressure transducer holder. In use, the support member may attach to a support surface, such as a housing of a power injection device, while the pressure transducer holder is moveably connected to the support member. The pressure transducer holder may expand open to receive one of a plurality of different sized pressure transducers and bias closed to hold a received one of the plurality of different sized pressure transducers. In addition, the pressure transducer holder may move relative to the support member to one of a plurality of different vertically elevated positions. The pressure transducer mounting device may accommodate different pressure transducers, providing a universal mounting device that can adapt to different medical provider preferences and different pressure transducer sourcing options.

21 Claims, 10 Drawing Sheets

(56) References Cited

U.S. PATENT DOCUMENTS

| | | | |
|---|---|---|---|
| 2,915,096 A | 12/1959 | Mooney | |
| 3,331,111 A | 7/1967 | Carver | |
| 3,996,927 A | 12/1976 | Frank | |
| 4,227,420 A * | 10/1980 | Lamadrid | A61B 5/0215 600/488 |
| 4,705,331 A | 11/1987 | Britton | |
| 4,901,964 A | 2/1990 | McConnell | |
| 4,920,966 A * | 5/1990 | Hon et al. | 600/459 |
| 4,970,907 A * | 11/1990 | Flynn | 73/866.5 |
| 5,146,816 A | 9/1992 | Badstieber | |
| 6,132,383 A * | 10/2000 | Chesney et al. | 600/502 |
| 7,520,007 B2 | 4/2009 | Skripps | |
| 7,703,358 B2 | 4/2010 | Ubinana | |
| 7,966,703 B2 | 6/2011 | Ubinana | |
| 2006/0290076 A1 | 12/2006 | Lees | |
| 2007/0107532 A1* | 5/2007 | Naslund et al. | 73/856 |
| 2007/0142717 A1* | 6/2007 | Lowery et al. | 600/323 |
| 2008/0058720 A1 | 3/2008 | Spohn et al. | |
| 2009/0121405 A1* | 5/2009 | Brown | B23K 37/0435 269/216 |
| 2010/0108841 A1 | 5/2010 | Kronner et al. | |
| 2013/0345528 A1* | 12/2013 | Kall | 600/310 |
| 2015/0041604 A1* | 2/2015 | Dihlmann | 248/292.12 |

FOREIGN PATENT DOCUMENTS

| | | |
|---|---|---|
| CN | 201643276 U | 11/2010 |
| EP | 0919181 A2 | 6/1999 |
| WO | 2010054836 A2 | 5/2010 |
| WO | 2010056528 A1 | 5/2010 |

OTHER PUBLICATIONS

Chapter II Demand and Amendments Under Article 34 and Response to Written Opinion filed Oct. 18, 2013 for PCT/US2013/038649, 22 pages.

Notification of Transmittal of International Search Report and Written Opinion of the International Search Authority, or the Declaration, Jul. 19, 2013, 9 pages, European Patent Office, Rijswijk, The Netherlands.

* cited by examiner

Fig. 1

UNIVERSAL PRESSURE TRANSDUCER MOUNTING DEVICE

TECHNICAL FIELD

This disclosure relates to medical pressure transducers and, more particularly, to medical pressure transducer mounting devices.

BACKGROUND

Pressure transducers are used in a variety of different industries for a variety of different applications. In the medical industry, for instance, pressure transducers are used to monitor bodily fluid pressures before, during, and after medical procedures. Information about bodily fluid pressures, such as blood pressure, can help a health care provider diagnose a condition of the patient. In some applications, the health care provider can also use the bodily fluid pressure information to adjust therapeutic treatments or diagnostic agents being delivered to the patient.

Angiography is one type of medical procedure that is typically performed while monitoring the blood pressure of a patient. Angiography is a procedure used to help diagnose and treat cardiovascular conditions including, for example, abnormalities or restrictions in blood vessels in the heart. During angiography, radiographic contrast media is injected through a catheter into a vein or artery, which then passes to vascular structures in fluid communication with the vein or artery. When X-rays are passed through the region of the body into which the contrast media is injected, the X-rays may be absorbed by the contrast media, providing radiographic images of the desired vascular structure(s).

To monitor the blood pressure of a patient during a medical procedure, such as angiography, the patient may be connected to a pressure transducer positioned outside of the body of the patient. For example, the pressure transducer may be hydraulically coupled to the patient's circulatory system via a catheter introduced inside the body of the patient. The catheter may hydraulically communicate pressure from within the body of the patient to the pressure transducer positioned outside of the body of the patient, which may then convert the hydraulic pressure to electrical signals for analysis, display, storage, etc.

Ensuring that a pressure transducer is properly oriented and positioned relative to a portion of the patient's body during a medical procedure may help ensure that the pressure transducer provides an accurate pressure reading. For example, when a patient is undergoing an angiographic procedure, the pressure transducer may be positioned within the same horizontal plane as the patient's heart. If the pressure transducer is positioned higher or lower than the horizontal plane containing the patient's heart, the weight of the column of fluid hydraulically connecting the pressure transducer to the patient's body may increase or decrease relative to when the pressure transducer is at a desired vertical position. In turn, this additional fluid weight may impact the accuracy of the blood pressure determined by the pressure transducer.

While a medical procedure room may include a permanent fixture for holding and positioning a pressure transducer relative to a patient's body, different size patients may dictate different pressure transducer positions. Further, medical care providers, such as doctors, often have significant amounts of discretion to choose the specific hardware they want to use when performing a medical procedure. In instances in which different medical care providers share a common medical procedure space, each medical care provider may use a different type or brand of pressure transducer when performing procedures.

SUMMARY

In general, this disclosure is directed to devices and techniques for mounting a pressure transducer so that the pressure transducer can be used to determine a patient's bodily fluid pressure before, during, and/or after a medical procedure. In some examples as described herein, a pressure transducer mounting device is configured to receive and hold a plurality of different types pressure transducers. For example, the pressure transducer mounting device may include a pressure transducer holder that expands in one direction (e.g., open or closed) to receive one of a plurality of different pressure transducers, where each of the plurality of different pressure transducers has a different size, shape, and/or connection features, and biases in an opposite direction (e.g., closed or open) to hold the specific transducer inserted into the pressure transducer holder. In an additional example, the pressure transducer mounting device includes at least two different pressure transducer holders that are each designed to receive and hold a different type of pressure transducer having different connection features. In use, a medical care provider can select a specific pressure transducer for use during a medical procedure from one of multiple different pressure transducer designs (e.g., which may be supplied from different pressure transducer manufacturers). Different pressure transducer designs may have different sizes, shapes, and/or different attachment structures for interfacing with a pressure transducer holder. However, by configuring the pressure transducer mounting device to receive different types of pressure transducers, the health care provider may insert the selected pressure transducer into the pressure transducer holder regardless of the design of the specific pressure transducer (e.g., the design of the specific attachment interface structure of the pressure transducer). In this way, the pressure transducer mounting device may accommodate different pressure transducers, providing a universal mounting device that can adapt to different medical provider preferences and different pressure transducer sourcing options.

Depending on the application, the pressure transducer mounting device may include a fixed portion that is connectable to a surface in a medical procedure space (e.g., a catheter lab) and a moveable portion that can move relative to the fixed portion. The moveable portion may include one or more pressure transducer holders that are configured to receive and hold pressure transducers having a variety of different designs. The moveable portion of the pressure transducer mounting device may be selectively moveable to different vertically elevated positions. In use, a health care provider may move the moveable portion and, hence, a pressure transducer connected to the moveable portion, to different vertical positions. This may be useful, for example, when the health care provider desires to position a pressure transducer relative to a specific anatomical landmark of patient.

In one example, a pressure transducer mounting device is described that includes a support member configured to attach to a support surface and a pressure transducer holder moveably connected to the support member. According to the example, the pressure transducer holder is configured to expand open to receive one of a plurality of different sized pressure transducers and bias closed to hold a received one of the plurality of different sized pressure transducers. In addition, the example specifies that the pressure transducer holder is configured to move relative to the support member to one of a plurality of different vertically elevated positions.

In another example, a system is described that includes a power injection device, a selected pressure transducer, and a pressure transducer mounting device. The power injection device includes a syringe configured to be driven by an electrical power source, at least one fluid reservoir in fluid communication with the syringe, and a tubing system configured to deliver fluid from the at least one fluid reservoir to a patient line. The selected pressure transducer is configured to monitor a hemodynamic pressure of a body of a patient and is also configured to be in fluid communication with the patient during operation of the power injection device. According to the example, the pressure transducer mounting device includes a support member attached to the power injection device and a pressure transducer holder moveably connected to the support member. The pressure transducer holder is configured to expand open to receive one of a plurality of different sized pressure transducers and bias closed to hold the selected pressure transducer. In addition, the example specifies that the pressure transducer holder is configured to move relative to the support member to one of a plurality of different vertically elevated positions.

In another example, a method is described that includes attaching a support member of a pressure transducer mounting device to a support surface. The method also includes expanding a pressure transducer holder moveably connected to the support member open to receive one of a plurality of different sized pressure transducers and biasing the pressure transducer closed to hold a received one of the plurality of different sized pressure transducers. According to the example, the pressure transducer holder is configured to move relative to the support member to one of a plurality of different vertically elevated positions.

In another example, a pressure transducer mounting device is described that includes means for attaching to a support surface and means for receiving and holding one of a plurality of different sized pressure transducers, where the means for receiving and holding is configured to receive and hold each of the different sized pressure transducers. According to the example, the means for receiving and holding is moveably connected to the means for attaching, and the means for receiving and holding is configured to move relative to the means for attaching to one of a plurality of different vertically elevated positions.

The details of one or more examples are set forth in the accompanying drawings and the description below. Other features, objects, and advantages will be apparent from the description and drawings, and from the claims.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes may be provided for selected elements, and all other elements employ that which is known to those of skill in the field. Those skilled in the art will recognize that many of the examples provided have suitable alternatives that can be utilized.

Invasive hemodynamic pressure monitoring can provide a continuous assessment of the status of a patient and their response to ongoing therapy or diagnostic analysis. Invasive hemodynamic pressure monitoring can yield information about the intra-arterial blood pressure of patient, pulmonary artery pressure, left atrial pressure, and/or central venous pressure of the patient. This information can then be used by a medical provider to help diagnose issues or adjust ongoing procedures being performed on the patient. For example, when delivering drugs or agents to a patient that affect the vascular system of the patient, medical providers often desire to monitor a patient's intra-arterial blood pressure.

To monitor the hemodynamic pressure of a patient, the patient may be catheterized and the catheter then coupled via a tube to a medical pressure transducer positioned outside of the body of the patient. The tube may be filled with a fluid (e.g., saline, blood) to hydraulically communicate pressure from within the patient's body to the transducer positioned outside of the body. Depending on the configuration, the pressure transducer may convert the hydraulic pressure to an electrical signal that can be analyzed, displayed, stored, or otherwise processed.

Overtime, many health care providers have developed preferences for different types of pressure transducers. Be it the manufacturer of the pressure transducer, the ease of use of a specific pressure transducer, cost, or other factors, individual health care providers may wish to use a specific brand or even model of pressure transducer when performing a procedure. In instances in which different health care providers share a common medical procedure space or common medical equipment, it would be useful if the space and/or equipment could accommodate the different types of pressure transducers that may be used by different personnel.

In accordance with the techniques described in this disclosure, a pressure transducer mounting device is described that may receive and hold a select one of any of a plurality of different types of pressure transducers, where different types of pressure transducers have different sizes, shapes, and/or different connection features for connecting to the pressure transducer mounting device. For example, the pressure transducer mounting device may include a pressure transducer holder that expands in one direction (e.g., open or closed) to receive one of any of a plurality of different types of pressure transducers and biases in an opposite direction (e.g., closed or open) to hold a specific transducer inserted into the pressure transducer holder. As another example, the pressure transducer mounting device may includes two different pressure transducer holders that are each designed to receive and hold a different type of pressure transducer having different connection features. The pressure transducer mounting device may accommodate different pressure transducers, providing a universal mounting device that can adapt to different medical provider preferences.

Example pressure transducers and pressure transducer mounting devices will be described in greater detail with reference to FIGS. 2-8. However, an example system that includes a powered contrast injector system and a pressure transducer will first be described with reference to FIG. 1.

Figure 1:
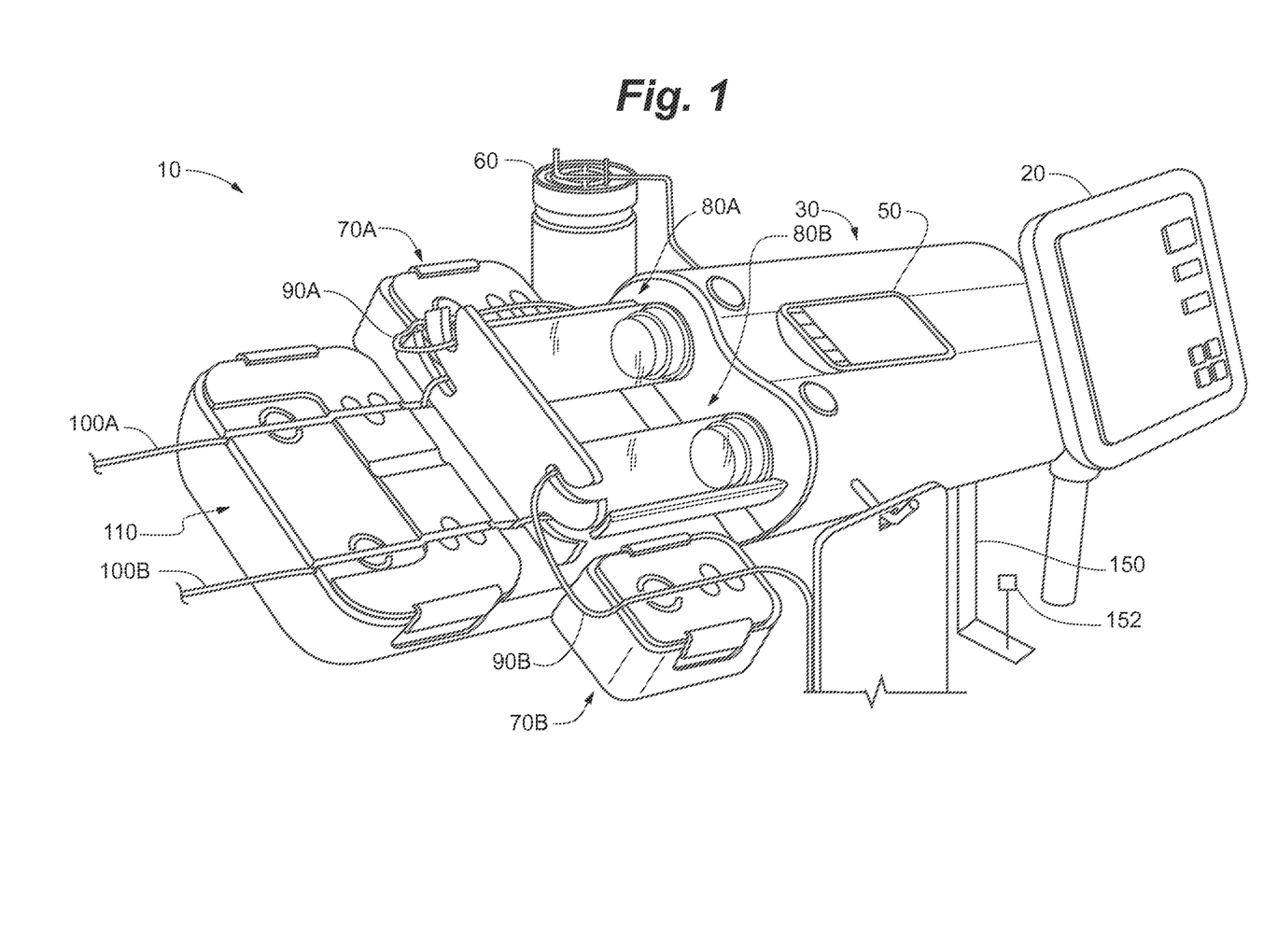
FIG. 1 is a perspective view of an example power injection system that may be used with a pressure transducer and a pressure transducer mounting device.

FIG. 1 is a perspective view of an example power injection system 10 that may be used with a pressure transducer and a pressure transducer mounting device, as described herein. Injection system 10 includes a dual-syringe injector system that has a main control panel 20, an injection head 30, and an electrical power supply (not shown). The electrical power supply may drive injection head 30. A first reservoir of medical fluid 60 is attached to the injection head 30, and a second reservoir of medical fluid 40 is also attached to the injection head 30. In some examples, the first reservoir 60 comprises a bottle of contrast media, and the second reservoir 40 comprises a bag of sterile diluent, such as saline.

In the example of injection system 10, the injection head 30 includes various subcomponents. For example, the injection head 30 includes a small control panel 50, first and second syringe/plunger assemblies 80A and 80B, first and second valve/air detection assemblies 70A and 70B, and assembly 110. The first and second syringe/plunger assemblies 80A and 80B each include a syringe chamber that houses a syringe and a plunger that is axially moveable through the syringe. Assembly 110 is positioned at a discharge end of first and second syringe/plunger assemblies 80A and 80B and may house various subcomponents of the system.

During operation, injection system 10 can draw fluid from the first reservoir 60 into the first syringe/plunger assembly 80A via tubing 90A by actuating a plunger to create a partial vacuum within the first syringe (i.e., by drawing the plunger back into injection head 30). Injection system 10 can also draw fluid from the second reservoir 40 into the second syringe/plunger assembly 80B via tubing 90B by actuating a second plunger to create a partial vacuum within the second syringe. By reversing the direction of plunger travel, injection system 10 can subsequently eject fluid out of the first syringe and/or second syringe of injection system 10 and through tube 100A and 100B, respectively, into a patient's body. In some examples, tube 100A and 100B are coupled to a patient line (e.g., via a three-way valve) that extends into a body of a patient. Injection system 10 can control the rate, volume, and source of fluid delivered to the patient, e.g., by controlling which plunger is actuated and the speed at which the plunger moves through a syringe.

It may be useful to monitor a patient's hemodynamic pressure during some injection procedures. For example, during angiography, a health care provider may record the intravascular and intra-cardiac pressures of the patient between injections of high pressure contrast media. The health care provider may look for pressure values falling within the general range of −1 psi to +6 psi (−51.7 mmHg to 310 mmHg) to confirm the hemodynamic health of the patient.

To monitor the hemodynamic pressure of the patient in these examples, injection system 10 may include a pressure transducer that is fluidly connected to the patient. In the example of FIG. 1, injection system 10 includes a pressure transducer 150 that is attached to the housing of injection head 30 via a pressure transducer mounting device 152. Pressure transducer 150 may be in fluid and/or pressure communication with a patient line extending into the patient (not illustrated in FIG. 1). During operation when the patient line (e.g., a catheter) is in place in the patient, pressure transducer 150 may monitor the hemodynamic pressure of the patient through a column of fluid which extends from the patient line to the pressure sensor, thereby providing patient hemodynamic data to injection system 10. Pressure transducer mounting device 152 may allow a health care provide to use a variety of different types of pressure transducers and/or properly orient pressure transducer 150 during operation of injection system 10, as described in greater detail below.

Figure 2:
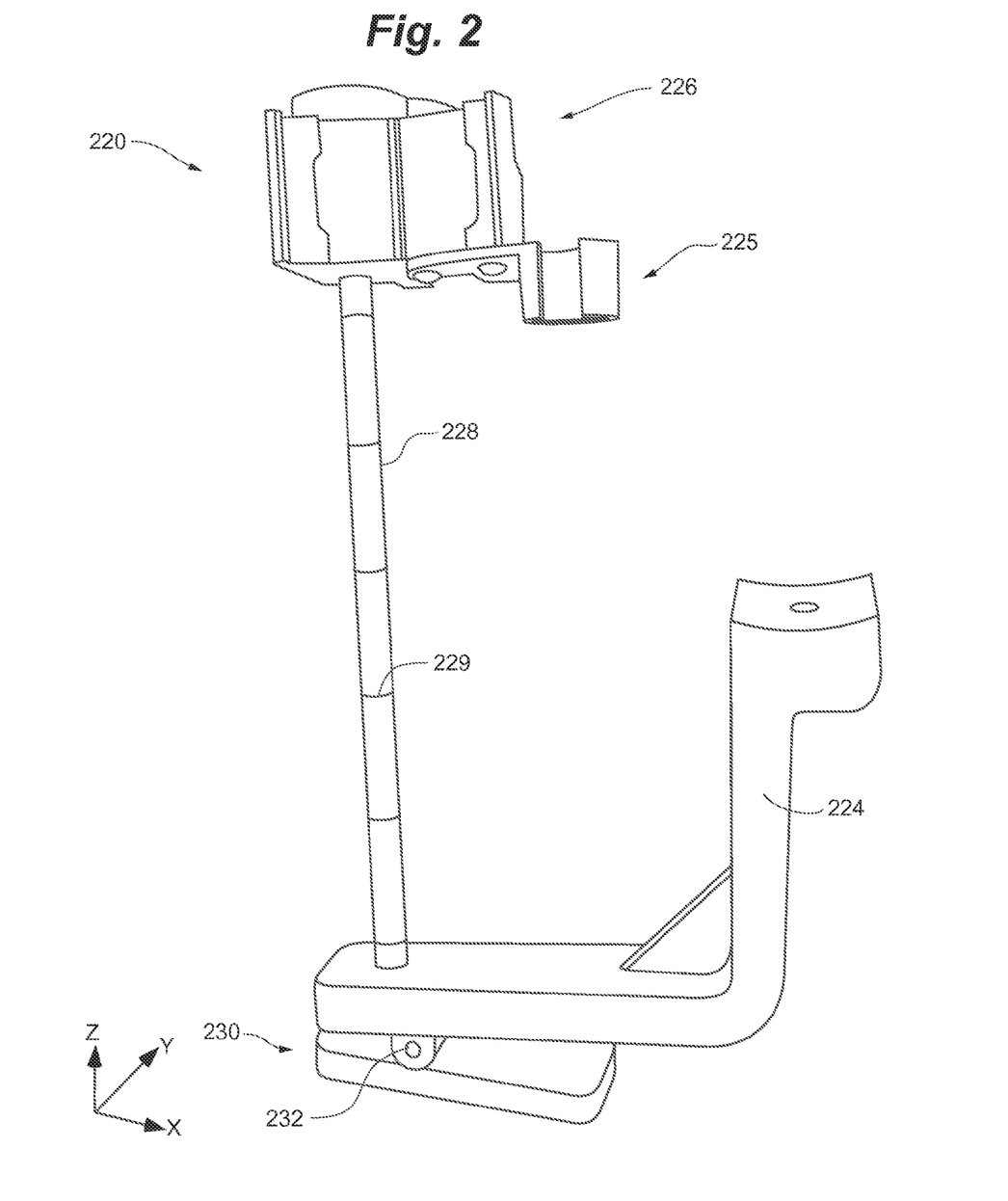
FIGS. 2 and 3 are different images of an example pressure transducer mounting device.
Figure 3:
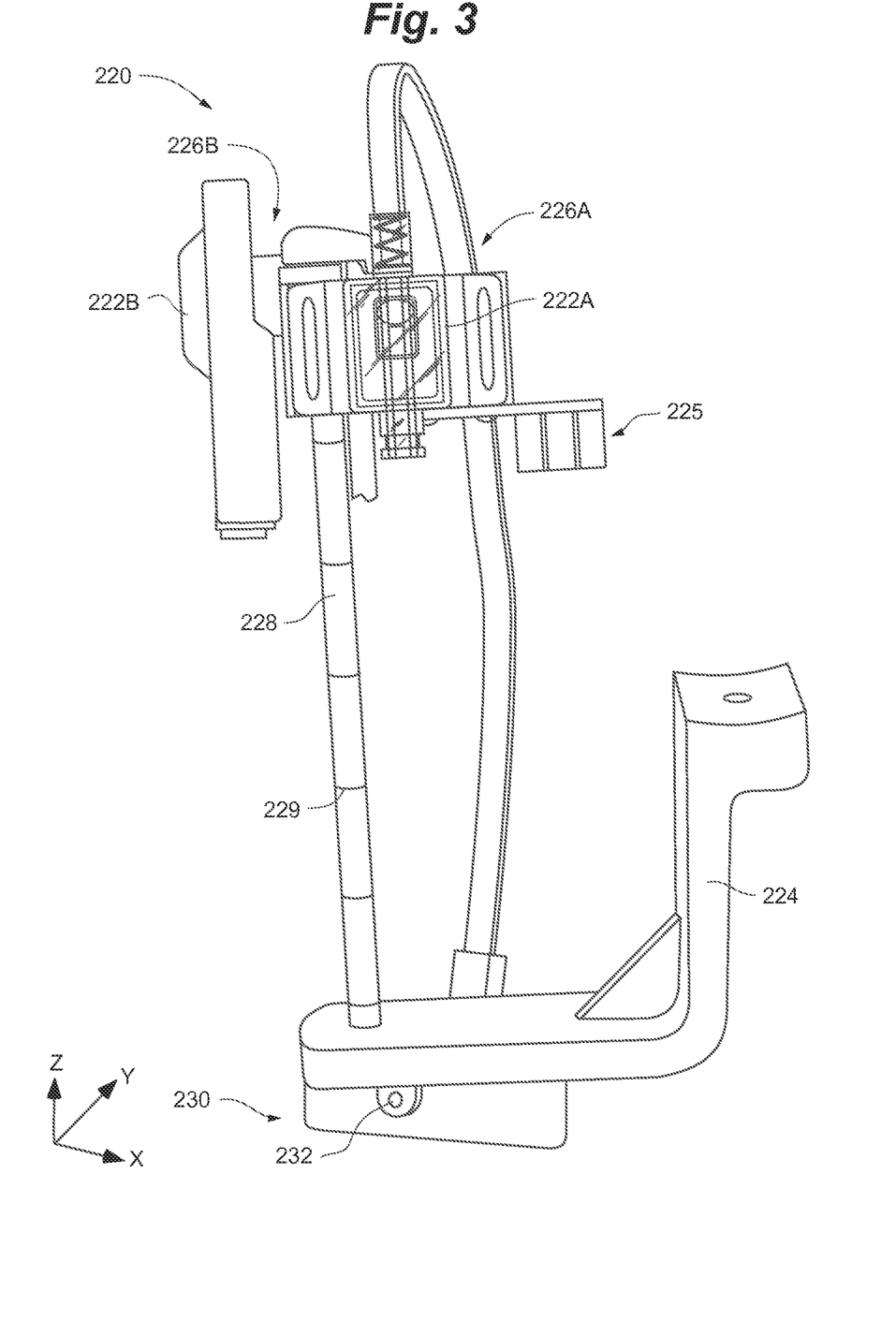

FIGS. 2 and 3 are different images of an example pressure transducer mounting device 220 (also referred to herein as "device 220") that may be used in injection system 10 (FIG. 1). FIG. 2 illustrates device 220 without a pressure transducer attached to the device. FIG. 3 illustrates device 220 with at least one pressure transducer attached to the device which, in the illustrated example, is shown as two pressure transducers: first pressure transducer 222A and second pressure transducer 222B (collectively "pressure transducer 222"). Device 220 includes a support member 224, a pressure transducer holder 226, and an elongated shaft 228. Pressure transducer holder 226 is connected to support member 224 via elongated shaft 228. Support member 224 is configured to attach to a support surface, such a housing of injection head 30 (FIG. 1), for positioning pressure transducer 222 to measure a bodily fluid pressure of a patient.

In addition, device 220 in FIGS. 2 and 3 includes a pressure equalization valve holder 225. In use, one or both of first pressure transducer 222A and second pressure transducer 222B may be connected to a patient line that hydraulically communicates pressure from within the body of the patient to the pressure transducer positioned outside of the body. During initial set up of the pressure transducer, a pressure equalization valve (e.g., a stop-cock) associated with the pressure transducer may be opened to expose the pressure transducer to atmospheric pressure. Opening the pressure equalization valve may calibrate the pressure transducer and/or remove trapped air. When device 220 includes pressure equalization valve holder 225, the pressure equalization valve holder may define a structure for receiving and holding a pressure equalization valve or a portion of tubing connected to a pressure equalization valve. In some examples, such as the example of FIGS. 2 and 3, pressure equalization valve holder 225 is positioned within substantially the same horizontal plane (e.g., the X-Y plane indicated in FIGS. 2 and 3) and/or at substantially the same vertical elevation (e.g., in the Z-direction indicated in FIGS. 2 and 3) as pressure transducer holder 226. Positioning pressure equalization valve holder 225 in substantially the same horizontal plane as pressure transducer holder 226 may help ensure that pressure transducer 222 is calibrated under the same fluid weight conditions as when the pressure transducer is subsequently used to measure bodily fluid pressure of a patient. In other examples, device 220 does not include pressure equalization valve holder 225.

As described in greater detail below, pressure transducer holder 226 is configured (e.g., sized and/or shaped) to receive and hold a plurality of different types of pressure transducers. A plurality of different types of pressure transducers may be, e.g., two, three, five, ten, or even more different types pressure transducers. In operation, a user may a select a specific pressure transducer 222 from the plurality of different sized pressure transducers and insert the selected pressure transducer into pressure transducer holder 226. Pressure transducer holder 226 may receive the selected pressure transducer 222 that is inserted into the holder and secure the pressure transducer during subsequent pressure monitoring operation. By configuring pressure transducer holder 226 to receive and hold a plurality of different types pressure transducers, a single pressure transducer mounting device 220 can be used to mount a variety of different types of pressure transducers for a medical procedure. For example, pressure transducer mounting device 220 may be used to mount pressure transducers supplied by different manufactures and/or different pressure transducer models supplied by a single manufacture rather than requiring different pressure transducer mounting devices for each different type of pressure transducer.

In some examples, device 220 includes a single pressure transducer mounting holder 226 that is configured to hold a plurality of different sized pressure transducers. In other examples, device 220 includes multiple pressure transducers holders that are each configured to hold different pressure transducers. Configuring device 220 with multiple pressure transducer holders may enable the device to attach to different types of pressure transducers having different types of connection features. For example, device 220 may include at least a first pressure transducer holder configured to attached to pressure transducers having a first type of connection features and a second pressure transducer holder configured to attach to pressure transducers having a second type of connection features different than the first type of connection features. When so configured, both pressure transducer holders may be configured to receive and hold pressure transducers having different types of attachment interface structures (e.g., different sized and/or shaped attachment interface structures).

In the example of FIGS. 2 and 3, device 220 includes two pressure transducer holders: first pressure transducer holder 226A and second pressure transducer holder 226B. First pressure transducer holder 226A is configured to receive and hold first pressure transducer 222A. Second pressure transducer holder 226B is configured to receive and hold second pressure transducer 222B. First pressure transducer holder 226A is circumferentially spaced from second pressure transducer holder 226B about a common axis extending through a center of elongated shaft 228. With this configuration, first pressure transducer holder 226A holds first pressure transducer 222A in a first plane (e.g., the X-Z plane indicated on FIG. 3) while second pressure transducer holder 226B holds second pressure transducer 222A in a second plane (e.g., the Y-Z plane indicated on FIG. 3) that is different than the first plane. This type of positioning may allow device 220 to simultaneously hold two different pressure transducers without having the pressure transducers compete for space. However, in other examples in which device 220 includes multiple pressure transducer holders, the pressure transducer holders may be arranged side-by-side (e.g., vertically or horizontally), opposite one another, or in any other suitable arrangement, and it should be appreciated that the disclosure is not limited in this respect.

Pressure transducer mounting device 220 holds pressure transducer 222. Pressure transducer 222 can be any device suitable for sensing a hemodynamic pressure (e.g., blood pressure) of a patient. In some examples, pressure transducer 222 is configured to generate a signal as a function of the pressure imposed on a portion of the transducer. In such examples, the transducer may include a flexible membrane that moves in response to pressure changes in a fluid in contact with the membrane. The transducer may then convert the sensed pressure to an electrical output signal (e.g., voltage and/or amperage) and transmit the signal to a pressure control module, a display, a computer readable storage medium, or the like. Although the operating parameters of pressure transducer 222 can vary, in some examples, the pressure transducer is rated to sense pressures ranging from approximately −30 mmHg to approximately 300 mmHg.

In one example, pressure transducer 222 is implemented as a piezoelectric pressure transducer. In general, a piezoelectric pressure transducer has a piezoelectric crystal that produces an electrical potential when placed under stress by a pressure-sensing element. Varying the amount of pressure on the pressure-sensing element varies the amount of stress and, hence, the electrical potential generated by the pressure transducer. In another example, pressure transducer 222 is implemented as a two component pressure sensor that includes a reusable sensor component and a disposable dome component. The reusable sensor component may include a diaphragm in pressure communication with a sensor while the disposable component includes a dome diaphragm that can be positioned in confronting, pressure-transmitting relationship with the diaphragm on the reusable sensor. In such examples, pressure transducer holder 226 may attach to the reusable sensor component which, in turn, connects to the disposable dome component. An example of such a two component pressure sensor is described in U.S. Pat. No. 5,848,971, the entire contents of which are incorporated herein by reference.

When device 220 is designed to simultaneously hold multiple different types of pressure transducers, each pressure transducer may be the same type of pressure transducer (e.g., a piezoelectric pressure transducer) but have different sizes, shapes, and/or connection features, or at least one pressure transducer (e.g., first pressure transducer 222A) may be a different type of pressure transducer than at least one other pressure transducer (e.g., second pressure transducer 222B). In one example, first pressure transducer 222A is a piezoelectric pressure transducer and second pressure transducer 222B is a two component pressure sensor that includes a reusable sensor component and a disposable component. Configuring device 220 to receive, or at least be capable of receiving, at least two different types of pressure sensors may be useful to increase the variety of sensors that a user can select to attach to device 220.

Pressure transducer holder 226 is connected support member 224. In particular, in the example of FIGS. 2 and 3, pressure transducer holder 226 is connected to support member 224 via elongated shaft 228. In some examples, pressure transducer holder 226 is fixedly connected to support member 224 so that the components cannot move relative to each other. In other examples, pressure transducer holder 226 is moveably connected to support member 224. When pressure transducer holder 226 is moveably connected to support member 224, a user may move the pressure transducer to one of multiple different positions relative to the support member and lock the pressure transducer in a desired position.

In the example of FIGS. 2 and 3, pressure transducer holder 226 is configured to move vertically (e.g., in the Z-direction indicated on FIGS. 2 and 3) to one of a plurality of different vertically elevated positions. Elongated shaft 228 is releasably locked in a specific vertically elevated position by locking mechanism 230. In operation, a user can disengage locking mechanism 230, slide elongated shaft 228 up or down to adjust the vertical position of pressure transducer holder 226, and then re-engage locking lock mechanism 230 so that the pressure transducer holder is held at a selected vertical position.

Configuring device 220 so that pressure transducer holder 226 is vertically moveable relative to support member 224 may be useful, e.g., to help accurately measure the hemodynamic pressure of a patient during a medical procedure. For example, when using pressure transducer 222 to monitor an intra-arterial blood pressure of a patient during a medical procedure, pressure transducer 222 may provide more accurate pressure determinations when positioned at the same or substantially the same vertical elevation as the patient's heart. This position, which may be referred to as a midaxial position, may vary based on the size of the specific individual undergoing the medical procedure. If pressure transducer 222 is positioned higher or lower than the horizontal plane containing the patient's heart, the weight of the column of fluid hydraulically connecting the pressure transducer to the patient's body may increase or decrease relative to when the pressure transducer is in the same horizontal plane as the patient's heart. This variation in fluid weight may impact the accuracy of pressure determinations made by pressure transducer 222. However, by configuring device 220 so that pressure transducer holder 226 is vertically movable relative to support member 224, a user can adjust the vertical height of pressure transducer 222, e.g., at the beginning of a medical procedure so that the pressure transducer is in the same or substantially the same horizontal plane as the heart of a patient undergoing the medical procedure.

When device 220 includes locking mechanism 230, the locking mechanism may be any feature that releasably locks pressure transducer holder 226 in a selected vertical position. In the example of FIGS. 2 and 3, locking mechanism is a beam that is pivotally connected to support member 224 about pivot 232. The beam includes an aperture that is aligned with an aperture extending through support member 224. When locking mechanism 230 is disengaged, the aperture of the beam is coaxially aligned with the aperture extending through support member 224 so that a distal portion of elongated shaft 230 can slide freely through both apertures (e.g., with a portion of the shaft position one side of the beam and support member and another portion of the shaft positioned on an opposite side of the beam and support member). Engaging locking member 230 causes a portion of the beam on one side of pivot 232 to bias away from support member 224, moving the aperture extending through the beam out of coaxially alignment with the aperture extending through support member 224. In turn, this may cause a portion of the beam to pinch elongated shaft 228, e.g., against a wall defining the aperture extending through the beam.

In the example of device 220, elongated shaft 228 includes vertical height indicia 229. Vertical height indicia 229 may be graphics or text that indicate the height between pressure transducer holder 226 and support member 224. Vertical height indicia 229 may provide a reference that allows a user to quickly adjust the vertical position of pressure transducer holder 226 relative to support member 224 to a desired location. In other examples, elongated shaft 228 does not include vertical height indicia 229. In addition, in different examples, elongated shaft 228 may or may not be completely removable from support member 224. Depending on the application, allowing a user to completely remove elongated shaft 228 from support member 224 may be helpful to provide access to features or equipment positioned pressure transducer holder 226.

To use pressure transducer mounting device 220, the device may be mounted to a support surface via support member 224 and then pressure transducer 222 inserted into pressure transducer holder 226. Support member may be any structure that can be attached pressure transducer holder 226 to a support surface so that the pressure transducer holder is spaced away from the support surface. In some examples, support member 224 is constructed of a rigid material that resists deformation during the use of device 220 such as metal or rigid thermoplastic. In addition, although support member 224 may be attached to a power injection device as described with respect to FIG. 1, in other examples, the support member may be attached to a different support surface such as, e.g., a patient bed rail, a wall of a procedure room, a moveable cart, or the like. Support member 224 can attach to a support surface using any suitable mechanical fixation element including, e.g., bolts, screws, adhesive, welding, and the like.

As briefly discussed above, first pressure transducer holder 226A of device 220 is configured to receive and hold a plurality of different sized pressure transducers. For example, first pressure transducer holder 226A may expand open to receive one of a plurality of different pressure transducers and bias closed to hold a selected pressure transducer that is inserted into the holder (e.g., while the holder is expanded open). Each of the plurality of different pressure transducers may have different sizes, shapes, and/or connection features.

Figure 4:
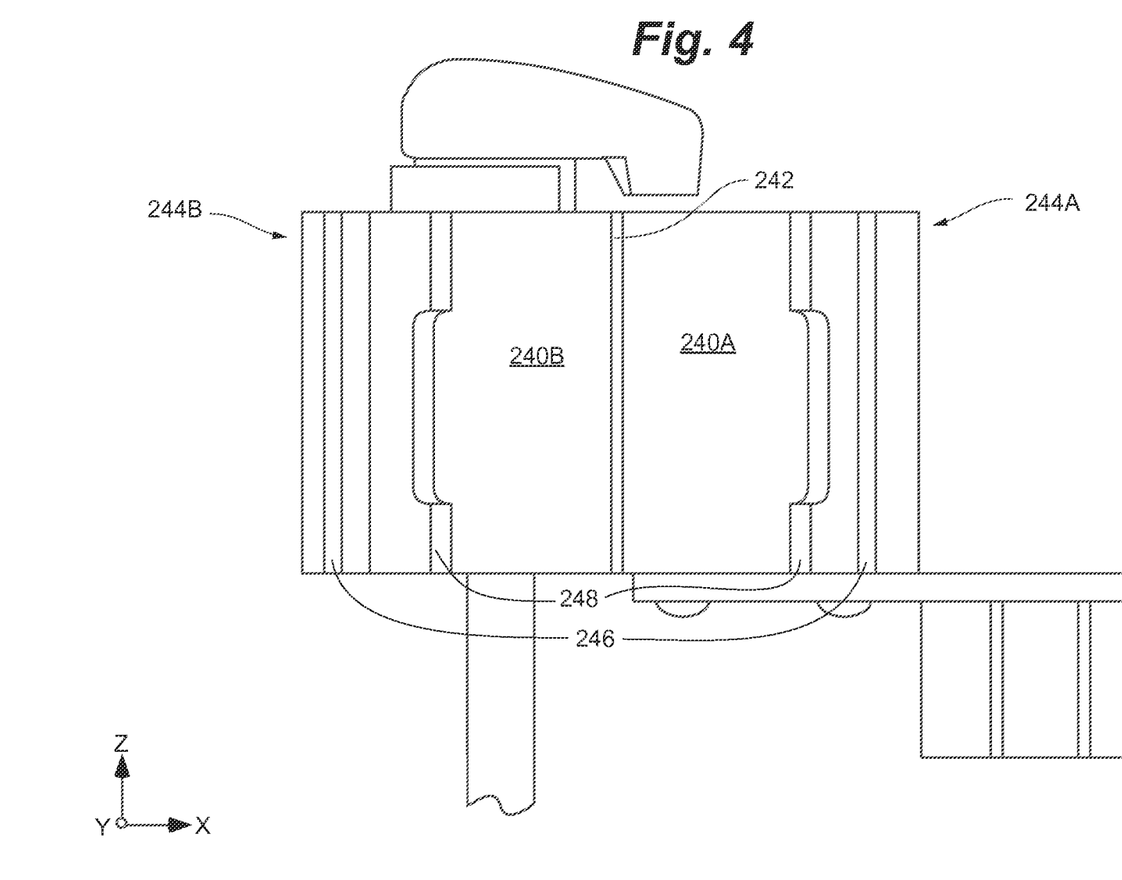
FIGS. 4 and 5 are exploded front and back images, respectively, showing an example configuration of a pressure transducer holder that may be used with pressure transducer mounting device of FIGS. 2 and 3.
Figure 5:
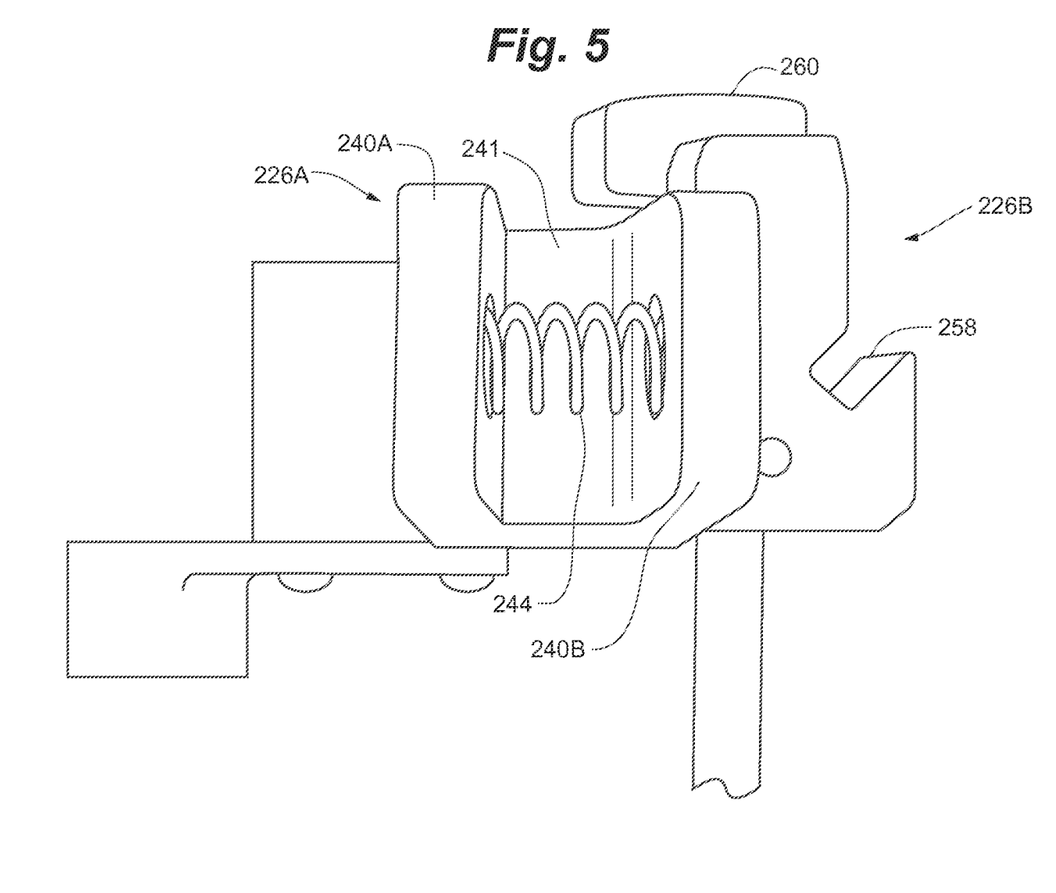

FIGS. 4 and 5 are exploded front and back images, respectively, showing an example configuration of first pressure transducer holder 226A. In this example, first pressure transducer holder 226 includes a first arm 240A and a second arm 240B that are pivotally connected about a pivot 241. First arm 240A and second arm 240B are biased toward each other to define an expandable front face (FIG. 4) that can expand open to receive a plurality of different size pressure transducers. To insert first pressure transducer 222A into first pressure transducer holder 226A, a user may press a back portion of first arm 240A toward a back portion of second arm 240B (FIG. 5). This action may cause a front portion of first arm 240A to pivot away from a front portion of second arm 240B (FIG. 4), creating an opening between the two arms at partition line 242. After inserting first pressure transducer 222A in the opening between first arm 240A and second arm 240B, the user can release the back portion of the two arms. Biasing member 244 may bias the front portion of first arm 240A toward the front portion of second arm 240B, closing the opening between the two arms. When biased closed with first pressure transducer 222A inserted into first pressure transducer holder 226A, first arm 240A and second arm 240B may each contact opposing sides of the pressure transducer so that the pressure transducer is held between the two arms.

To help hold first pressure transducer 222A between first arm 240A and second arm 240B of first pressure transducer holder 226A, the pressure transducer holder may include additional engagement surfaces for engaging with the pressure transducer. In the example of FIG. 4, first pressure transducer holder 226A includes first pressure transducer engagement surface 244A extending from first arm 240A and a second pressure transducer engagement surface 244B extending from second arm 240B. First pressure transducer engagement surface 244A and second pressure transducer engagement surface 244B define at least one pair of opposed channels that can engage opposing sides of first pressure transducer 222A. For example, first pressure transducer engagement surface 244A and second pressure transducer engagement surface 244B may each define a right-angled channel into which an edge of first pressure transducer 222A can be inserted.

In the example of FIG. 4, first pressure transducer engagement surface 244A and second pressure transducer engagement surface 244B define two pairs of opposed channels: a first pair of opposed channels 246 and a second pair of opposed channels 248. The first pair of opposed channels 246 are spaced a first distance from one another while the second pair of opposed channels 248 are spaced a second distance from one another that is less than the first distance. In some examples, the first distance ranges from approximately 0.5 inches to approximately 1.25 inches when first arm 240A and second arm 240B are biased closed without a pressure transducer inserted between the arms. In such examples, the second distance may range from approximately 1.25 inches to approximately 2 inches when first arm 240A and second arm 240B are biased closed without a pressure transducer inserted between the arms. Depending on the design of first pressure transducer holder 226A, the first distance range and the second distance range may each increase by at least 5% when first arm 240A and second arm 240B are expanded open such as, e.g., at least 10%, at least 25%, or from approximately 5% to approximately 35%. Increasing the expansion range between first arm 240A and second arm 240B may increase the number of different sized pressure transducers that can be accommodated by first pressure transducer holder 226A.

Figure 6:
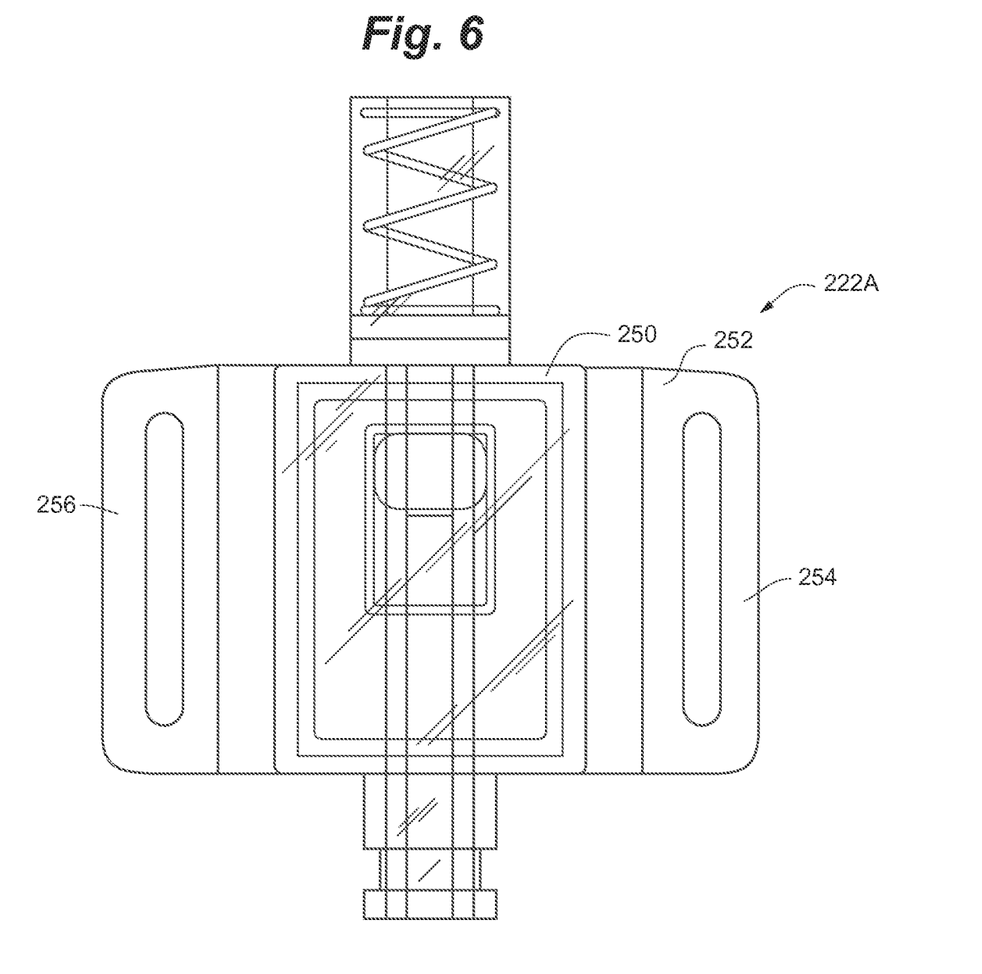
FIG. 6 is an image of an example pressure transducer that may be received and held by the example pressure transducer holder of FIGS. 4 and 5.

FIG. 6 is an image of an example first pressure transducer 222A that may be received and held by first pressure transducer holder 226A. First pressure transducer 222A in this example includes a piezoelectric pressure sensor element 250 mounted to a generally planar backing plate 252. The piezoelectric pressure sensor element 250 can be hydraulically coupled to a patient's circulatory system via a catheter introduced inside the body of the patient. Backing plate 252 can be inserted into first pressure transducer holder 226A, e.g., so that a first edge 254 of the backing plate is in a channel defined by first pressure transducer engagement surface 244A and a second edge 256 of the backing plate is in a channel defined by second pressure transducer engagement surface 244B. Although backing plate 250 in the example FIG. 6 is generally planar (e.g., residing within a single plane having a width approximately equal to the thickness of the plate), in other examples, backing plate 250 may not be planer. In addition, while backing plate 250 is illustrated as being rectangular, backing plate 250 can define any polygonal (e.g., square, hexagonal) or arcuate (e.g., circular, elliptical) shape, or even combinations of polygonal and arcuate shapes. The specific shape of backing plate 250 may vary, e.g., based on the model or specific manufacture of the pressure transducer. Therefore, although pressure transducer holder 226 of pressure transducer mounting device 220 is generally described as being able to receive a plurality of different sized pressure transducers, pressure transducer holder 226 may also receive a plurality of different shaped pressure transducers independent of the specific size of each pressure transducer.

Figure 7:
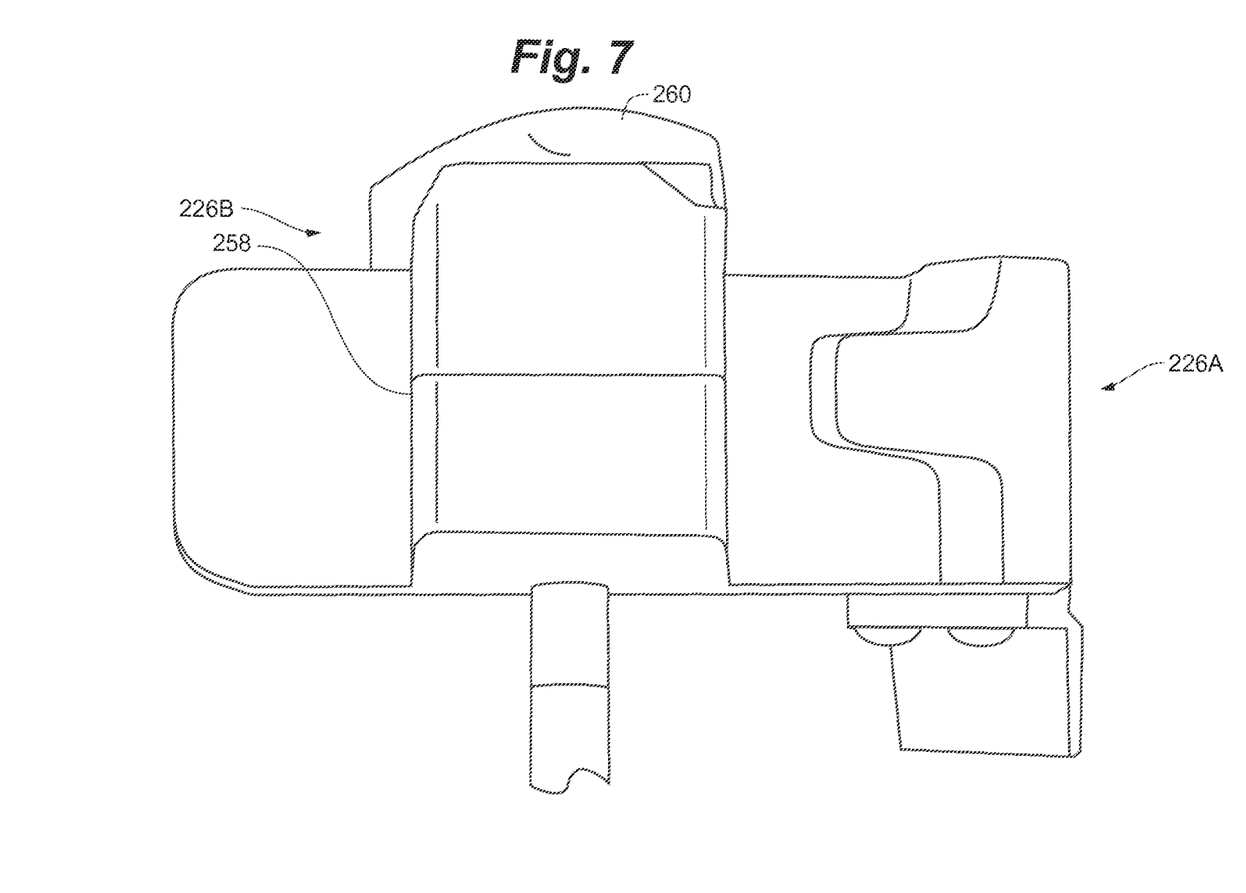
FIG. 7 is an image of another example pressure transducer holder that may be used with pressure transducer mounting device of FIGS. 2 and 3.

As briefly discussed above, pressure transducer mounting device 220 includes a second pressure transducer holder 226B. FIG. 5 is a side image and FIG. 7 is a front image of an example configuration of second pressure transducer holder 226B. Second pressure transducer holder 226B defines a channel 258 that is configured to receive a bottom lip of second pressure transducer 222B. Second pressure transducer holder 226B also includes a locking member 252 that can rotate to engage a top lip of second pressure transducer 222B. In operation, a user may insert a bottom lip of second pressure transducer 222B into channel 258 and then rotate locking member 252 to engage a top lip of the pressure transducer so that the pressure transducer is held between channel 258 and locking member 252. In this way, second pressure transducer 222B may be received and held by second pressure transducer holder 226B.

Figure 8:
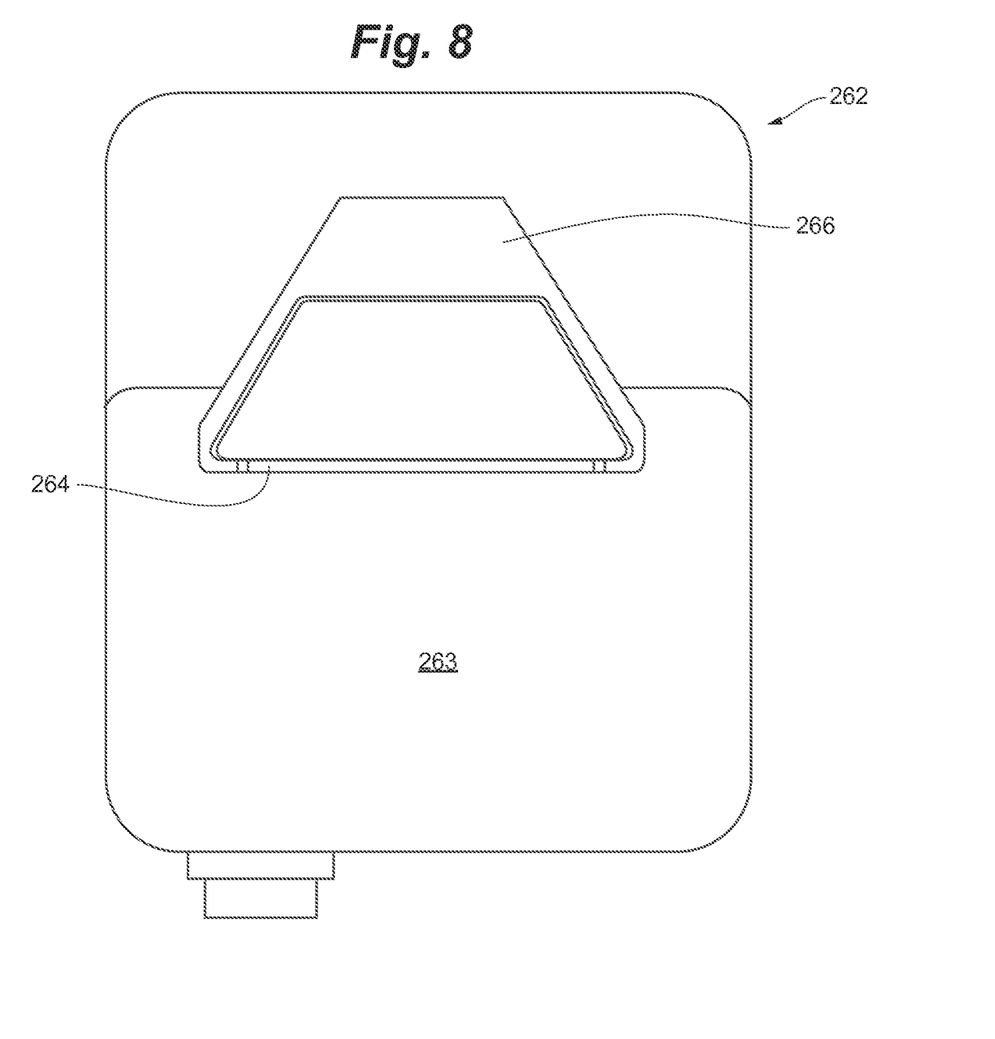
FIG. 8 is an image of an example pressure transducer that may be received and held by the example pressure transducer holder of FIG. 7.

FIG. 8 is an image of an example second pressure transducer 222B that includes a top lip and a bottom lip that may be inserted into second pressure transducer holder 226B. In particular, FIG. 8 is an image of a back side of an example reusable component 262 of a two part pressure transducer which, in combination with a disposable component (now shown) defines second pressure transducer 228. In this example, reusable component 262 defines an attachment projection projecting of a back surface 263 of the component. The attachment projection defines a bottom lip 264 and a top lip 266. In operation, a user may insert bottom lip 264 into channel 258 and then rotate locking member 252 over top lip 266 to hold reusable component between the channel and the locking member of second pressure transducer holder 226B.

With back surface 263 of reusable component 262 received and held by second pressure transducer holder 226B, one or more disposable components may be attached to a front surface of the reusable component to provide second pressure transducer 222B. In some examples, a front surface of reusable component 262 is designed to attach to only a single disposable component to provide a single pressure transducer. In other examples, the front surface of reusable component 262 is designed to attached to multiple (e.g., two, three, four, or more) disposable components to provide multiple pressure transducers, e.g., for measuring different pressures or the pressure of different bodily fluids. Regardless, when second pressure transducer holder 226B is designed to receive and hold a two-part pressure transducer, the pressure transducer holder may only directly receive and hold one part of the pressure transducer while the second part of the pressure transducer is subsequently connected to the part already held by second pressure transducer holder 226B. Therefore, although pressure transducer holders of device 220 are described herein as being configured to receive an hold a pressure transducer, the pressure transducer holders need not receive and hold an entire pressure transducer but may instead receive and hold only a portion or a part of the pressure transducer.

Pressure transducer mounting device 220 can have different configurations and/or can be used to other types of equipment in addition to or in lieu of what has been described above, as will be appreciated by those of skill in the art. For instance, in one example, pressure transducer mounting device 220 is designed to receive a laser leveling device to help a health care provider set pressure transducer holder 226 to a desired vertically elevated position. The laser leveling device may be attached to device 220 so that the laser leveling device is in the same or substantially the same horizontal plane as pressure transducer holder 226. With a laser dot pointed at a patient, the health care provider can move pressure transducer holder 226 up or down relative to support member 224 unit the laser dot is pointed at a desired anatomical landmark on the patient such as, e.g., a midaxial position on the patient. In this manner, the health care provider can use the laser leveling device to set the vertical position of pressure transducer holder 226 and, hence, a pressure transducer inserted into the pressure transducer holder.

Figure 9:
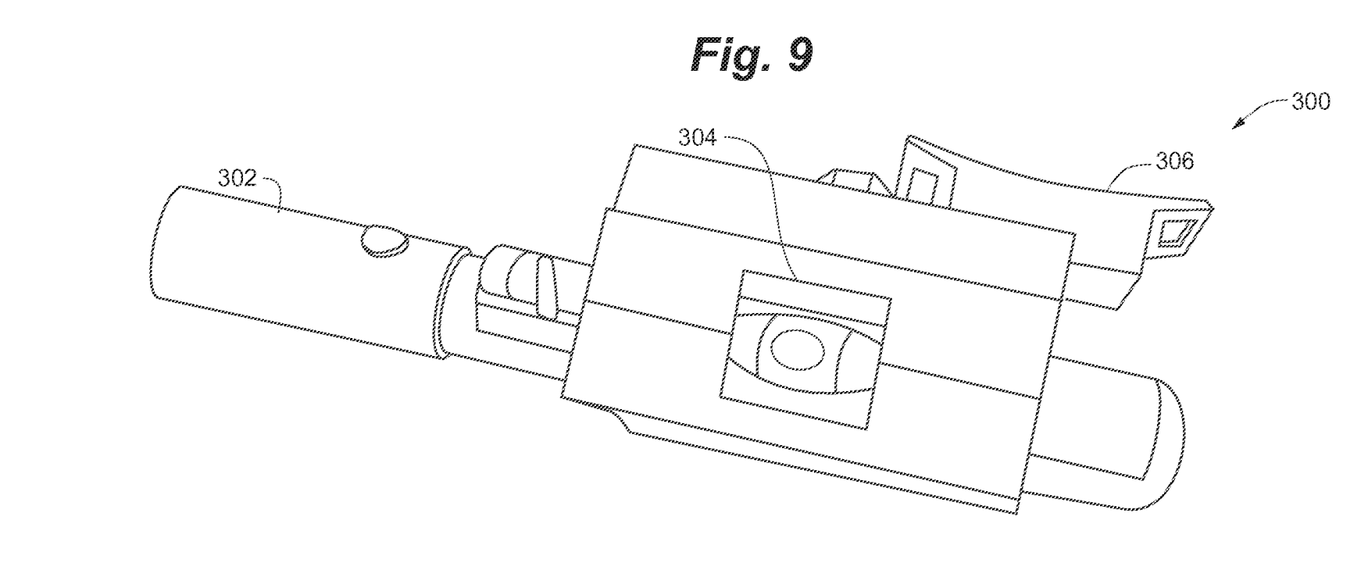
FIG. 9 is an image of an example laser leveling device that may be used with the pressure transducer mounting device of FIGS. 2 and 3.

FIG. 9 is an image of an example laser leveling device 300 that may be used with pressure transducer mounting device 220. Laser leveling device 300 includes a laser emitter 302, a bubble level 304, and a connector 306. Laser emitter 302 emits light that can be directed at a patient to define a laser pointer dot. Bubble level 304 provides a leveling indication for leveling laser emitter 302, e.g., when attaching laser leveling device 300 to device 220. For example, after attaching laser leveling device 300 to device 200, a user may reference bubble level 304 to adjust laser emitter 302 until the emitter is horizontal (e.g., directing light parallel to ground).

Figure 10:
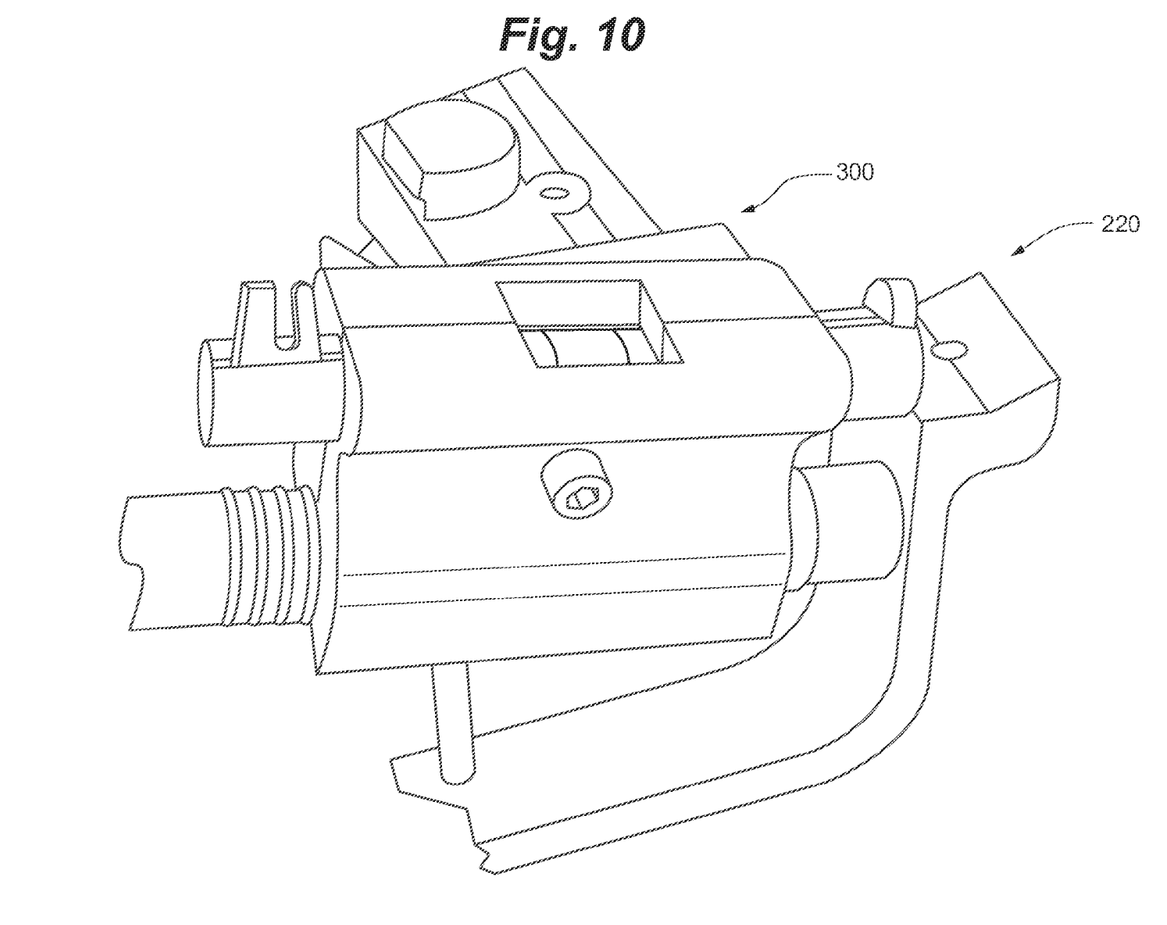
FIG. 10 is an image showing the example laser leveling device of FIG. 7 connected to an example pressure transducer mounting device.

Connector 306 can be used to connect laser leveling device 300 to device 220. In some examples, connector 306 has the same size, shape, and/or style as a portion of first pressure transducer 222A and/or second pressure transducer 222B that is received and held by first pressure transducer holder 226A and/or second pressure transducer holder 226B. For example, connector 306 may define the same size and/or shape as backing plate 252 of first pressure transducer 222A (FIG. 6) and/or the attachment projection of second pressure transducer 222B (FIG. 8) that defines bottom lip 264 and top lip 266. When so configured, connector 306 of laser leveling device 300 can be inserted into and held by first pressure transducer holder 226A and/or second pressure transducer holder 226B. FIG. 10 is an image showing an example of laser leveling device 300 connected to pressure transducer mounting device 220 via first pressure transducer holder 226A.

Various examples have been described. These and other examples are within the scope of the following claims.

The invention claimed is:

1. A pressure transducer mounting device comprising:
a support member configured to attach to a support surface; and
a pressure transducer holder moveably connected to the support member, the pressure transducer holder comprising a first arm and a second arm that are pivotally connected about a pivot, wherein a front portion of the first arm is configured to pivot away from a front portion of the second arm to expand open to receive one of a plurality of different sized pressure transducers, and the front portion of the first arm is biased to pivot toward the front portion of the second arm to hold a received one of the plurality of different sized pressure transducers, and
wherein the pressure transducer holder is configured to move relative to the support member to one of a plurality of different vertically elevated positions.

2. The pressure transducer mounting device of claim 1, wherein the support surface is a housing of a power injection device.

3. The pressure transducer mounting device of claim 1, wherein the pressure transducer holder further comprises a first pressure transducer engagement surface extending from the first arm and a second pressure transducer engagement surface extending from the second arm, the first pressure transducer engagement surface and the second pressure transducer engagement surface defining opposed channels configured to engage opposing sides of the received one of the plurality of different sized pressure transducers.

4. The pressure transducer mounting device of claim 3, wherein the first pressure transducer engagement surface and the second pressure transducer engagement surface define a first pair of opposed channels spaced a first distance from one another and a second pair of opposed channels spaced a second distance from one another, the first distance being greater than the second distance such that a larger pressure transducer can be engaged between the first pair of opposed channels than the second pair of opposed channels.

5. The pressure transducer mounting device of claim 4, wherein the first distance ranges from approximately 0.5 inches to approximately 1.25 inches and the second distance ranges from approximately 1.25 inches to approximately 2 inches.

6. The pressure transducer mounting device of claim 1, wherein the pressure transducer holder comprises a first pressure transducer holder, and further comprising a second pressure transducer holder spaced circumferentially from the first pressure transducer holder about a common axis to which both the first pressure transducer holder and the second pressure transducer holder are attached.

7. The pressure transducer mounting device of claim 6, wherein the first pressure transducer holder is configured to hold a first pressure transducer in a first plane and the second pressure transducer holder is configured to hold a second pressure transducer in a second plane different from the first plane.

8. The pressure transducer mounting device of claim 6, wherein the second pressure transducer holder defines a channel configured to receive a bottom lip of a pressure transducer and a locking member configured to engage a top lip of the pressure transducer so as to secure the pressure transducer between the channel and the locking member.

9. The pressure transducer mounting device of claim 1, wherein the pressure transducer holder comprises an elongated shaft and the support member comprises an aperture, the pressure transducer holder being moveably connected to the support member by inserting a distal portion of the elongated shaft through the aperture and pinching the elongated shaft against a wall defining the aperture.

10. The pressure transducer mounting device of claim 1, further comprising a pressure equalization valve holder connected to the pressure transducer holder such that the pressure equalization valve holder is positioned within substantially a same horizontal plane as the pressure transducer holder, the pressure equalization valve holder being configured to receive a valve in fluid communication with the received one of the plurality of different sized pressure transducers for calibrating the pressure transducer.

11. The pressure transducer mounting device of claim 1, further comprising a laser leveling device connected via the pressure transducer holder.

12. A method comprising:
expanding a pressure transducer holder of a pressure transducer mounting device that is moveably connected to a support member open to receive one of a plurality of different sized pressure transducers by pivoting a front portion of a first arm of the pressure transducer holder away from a front portion of a second arm of the pressure transducer holder and biasing the front portion of the first arm toward the front portion of the second arm to hold a received one of the plurality of different sized pressure transducers,
wherein the pressure transducer holder is configured to move relative to the support member to one of a plurality of different vertically elevated positions.

13. The method of claim 12, further comprising attaching the support member to a support surface.

14. The method of claim 12, wherein the pressure transducer holder further comprises a first pressure transducer engagement surface extending from the first arm and a second pressure transducer engagement surface extending from the second arm, the first pressure transducer engagement surface and the second pressure transducer engagement surface defining opposed channels configured to engage opposing sides of the received one of the plurality of different sized pressure transducers.

15. The method of claim 14, wherein the first pressure transducer engagement surface and the second pressure transducer engagement surface define a first pair of opposed channels spaced a first distance from one another and a second pair of opposed channels spaced a second distance from one another, the first distance being greater than the second distance such that a larger pressure transducer can be engaged between the first pair of opposed channels than the second pair of opposed channels.

16. The method of claim 12, wherein the pressure transducer holder comprises a first pressure transducer holder, and further comprising a second pressure transducer holder spaced circumferentially from the first pressure transducer holder about a common axis to which both the first pressure transducer holder and the second pressure transducer holder are attached.

17. The method of claim 16, wherein the second pressure transducer holder defines a channel configured to receive a bottom lip of a pressure transducer and a locking member configured to engage a top lip of the pressure transducer so as to secure the pressure transducer between the channel and the locking member.

18. The method of claim 12, wherein the pressure transducer holder comprises an elongated shaft and the support member comprises an aperture, and further comprising inserting a distal portion of the elongated shaft through the aperture and pinching the elongated shaft against a wall defining the aperture so as to moveably connect the pressure transducer holder to the support shaft.

19. The method of claim 12, further comprising inserting a valve in fluid communication with the received one of the plurality of different sized pressure transducers in a pressure equalization valve holder connected to the pressure transducer holder, the pressure equalization valve holder being positioned within substantially a same horizontal plane as the pressure transducer holder, and opening the valve so as to calibrate the received one of the plurality of different sized pressure transducers.

20. A pressure transducer mounting device comprising:

means for attaching to a support surface; and means for receiving and holding one of a plurality of different sized pressure transducers, the means for receiving and holding comprising a first arm and a second arm pivotally connected about a pivot and being configured to receive and hold each of the different sized pressure transducers, wherein the means for receiving and holding is moveably connected to the means for attaching, and wherein the means for receiving and holding is configured to move relative to the means for attaching to one of a plurality of different vertically elevated positions.

21. The pressure transducer mounting device of claim 20, wherein the means for receiving and holding comprise a first means for receiving and holding that is configured to receive and hold a first pressure transducer that is mounted to a generally planar backing plate and a second means for receiving and holding that is configured to receive and hold a second pressure transducer that has an attachment projection defining a top attachment lip and a bottom attachment lip.

* * * * *